United States Patent [19]

Turanchik et al.

[11] Patent Number: 4,547,466

[45] Date of Patent: Oct. 15, 1985

[54] DETECTING RHEUMATOID FACTOR WITH SYNTHETIC PARTICLES HAVING IMMUNE COMPLEXES THEREON

[75] Inventors: Michael F. Turanchik, Rockland County, N.Y.; Kwok K. Yeung, Malvern, Pa.; Nathan L. Smith, North Andover, Ma.

[73] Assignee: Allied Corporation, Morris Township, Morris County, N.J.

[21] Appl. No.: 499,957

[22] Filed: Jun. 1, 1983

[51] Int. Cl.$^4$ ............................................. G01N 33/54
[52] U.S. Cl. ................................... 436/509; 436/507; 436/533; 436/534; 436/808
[58] Field of Search ............... 436/509, 513, 533, 534, 436/506, 507

[56] References Cited

U.S. PATENT DOCUMENTS

| | | | |
|---|---|---|---|
| 4,143,124 | 3/1979 | Masson et al. | 436/513 |
| 4,279,617 | 7/1981 | Masson et al. | 436/509 |
| 4,283,383 | 8/1981 | Masson et al. | 436/509 |
| 4,332,783 | 6/1982 | Pernice et al. | 436/506 |
| 4,427,781 | 1/1984 | Masson et al. | 436/509 |

OTHER PUBLICATIONS

Chemical Abstracts, I, 98: 50011y (1983).
J. M. Singer, "The Latex Fixation Test in Rheumatic Diseases" Am. J. of Med., vol. 31, pp. 766–779 (1981).
J. M. Singer et al., "Performance of Latex-Fixation Kits Used for Serologic Diagnosis of Rheumatoid Factor in Rheumatoid Arthritis Sera" Am. J. Clin. Path., vol. 72, No. 4, pp. 597–603, Oct. 1979.

*Primary Examiner*—Sidney Marantz
*Assistant Examiner*—L. Krawczewicz
*Attorney, Agent, or Firm*—Alan M. Doernberg

[57] ABSTRACT

A suspension of particles such as carboxylated polystyrene latex particles are coated (as by carbodiimide coupling) with an antigen (such as chemically modified Bovine Serum Albumin). The antigen-coated particles are incubated with a gamma-globulin to the antigen (such as can be produced by immunizing rabbits) under non-agglutinating conditions. The particles having antigen/gamma-globulin immune complexes are recovered and resuspended to form a diagnostic reagent which agglutinates when mixed with human serum containing Rheumatoid Factor.

38 Claims, No Drawings

DETECTING RHEUMATOID FACTOR WITH SYNTHETIC PARTICLES HAVING IMMUNE COMPLEXES THEREON

BACKGROUND OF THE INVENTION

The present invention relates to a diagnostic reagent of the agglutination type for the detection of Rheumatoid Factor, a process for its preparation, a method for its use in qualitatively and quantitatively detecting the presence of Rheumatoid Factor and a kit for such detection including such diagnostic reagent.

Rheumatoid Factor (RF) is an autoantibody directed against human or animal gamma-globulins, and especially against the Fc portion of human or animal IgG. The autoantibody itself may be one of several immunoglobulin classes (IgM, IgG and IgA), with the class most often detected in tests for RF being IgM due to its superior agglutination reactions due to its highly multivalent binding characteristics. The presence of RF in human serum is not necessarily indicative of rheumatoid arthritis since RF is present in normal populations and, increasingly, in patients having other diseases such as SLE, infectious mononucleosis and various viral infections. Existing reagents and kits for the detection of RF factor fall into two classes: Synthetic particles coated with IgG (generally by absorption) and erythrocytes (especially sheep erythrocytes) coated with antierythrocyte antibodies (generally of the IgG type), suspended in either instance in a storage-stable medium. The antibody-coated particle reagents have the disadvantage of less specificity than the erythrocyte type because of clumping in the absence of RF and because of agglutination (a positive test) with RF levels so low as to be found in the general population. The erythrocyte-type reagents and kits have the disadvantages of relatively large particles (5–8 micrometers) which can cause grainy suspensions even in the absence of RF in the sample, false positives due to antibodies to infectious mononucleosis in the serum analyzed (which cross-reacts with erythrocytes antigens) and generally low sensitivity (cannot detect the lowest levels of RF concentration in serum samples).

BRIEF DESCRIPTION OF THE INVENTION

The present invention is based upon the use of synthetic particles having coated thereon immune complexes of antigens and gamma-globulins directed against the antigens, which agglutinate in a rapid fashion upon incubation with serum samples containing Rheumatoid Factor (RF). The present invention includes a process for preparing the reagent, the diagnostic reagent, a method of testing for RF and a diagnostic kit for conducting such method. Thus, the invention includes a process for preparing a diagnostic reagent for Rheumatoid Factor which comprises the steps:

(a) attaching to suspendable synthetic particles an antigen to form particles having multiple active antigen sites, (b) incubating a suspension of said particles having multiple active antigen sites with a solution containing a gamma-globulin to the antigen under conditions forming a substantially non-agglomerated suspension of particles having multiple antigen/gamma-globulin immune complexes thereon which are active as antigens to Rheumatoid Factor as antibody, (c) recovering said particles having multiple antigen/gamma-globulin immune complexes thereon from suspension, and (d) resuspending said particles having multiple antigen/gamma-globulin immune complexes thereon in a storage-stable medium.

The invention also includes a diagnostic reagent for Rheumatoid Factor comprising a suspension in a storage-stable medium of a plurality of synthetic particles having multiple antigen/gamma-globulin immune complexes thereon wherein the antigen is attached to the synthetic particle and wherein the antigen/gamma-globulin immune complexes are effective as antigens to Rheumatoid Factor as antibody.

The present invention also includes a diagnostic method for the detection of Rheumatoid Factor in a serum sample which comprises incubating the serum sample with a plurality of synthetic particles having multiple antigen/gamma-globulin immune complexes thereon wherein the antigen is attached to the synthetic particle and wherein the antigen/gamma-globulin immune complexes are effective as antigens to Rheumatoid Factor as antibody, whereby the particles will agglomerate if a sufficient quantity of Rheumatoid Factor is present in the serum sample.

The present invention also includes a diagnostic kit for practicing the diagnostic method, which kit includes the diagnostic reagent of the present invention and a positive control solution containing Rheumatoid Factor. The diagnostic kit preferably also contains a negative control solution substantially free of Rheumatoid Factor and, optionally, a diluent solution for diluting aliquots of serum samples to different dilution levels before incubating with an aliquot of said diagnostic reagent.

DETAILED DESCRIPTION OF THE INVENTION

We will now describe the novel process of preparing a diagnostic reagent, then the diagnostic reagent, then the novel method of testing for Rheumatoid Factor and finally the novel kit for practicing this method. Each novel aspect of the invention is preferably used for and in conjunction with the others (e.g, the method is preferably conducted with the novel reagent prepared by the novel process). It should be appreciated, however, that these interrelationships are not essential in that, for example, the recovered particles of step (c) of the process could be suspended directly in test serum without preparing the novel reagent or kit or practicing the resuspension step (d) of the novel process. Such alternatives are considered to be within the scope of the invention as defined by at least one form thereof, but are generally not preferred.

The first step of the process of the invention is to attach an antigen to a synthetic particle to form particles having multiple active antigen sites. The particle used is considered "synthetic" in the sense of being abiological, and being essentially immunologically inactive. In this respect, it differs substantially from the sheep erythrocytes used in one type of prior art reagent. The particle may be polymeric, ceramic (e.g., bentonite), activated charcoal or cholesterollecithin, but is preferably polymeric and is preferably of the latex type. Preferred such particles are carboxylated polystyrene particles (carboxylated polystyrene latex particles), which are preferably of average diameter between about 0.2 and about 2 micrometers, with an average diameter between about 0.4 and about 1.5 micrometers being more preferred. These preferred and more preferred dimensions apply: (1) to particles generally, (2) to latex particles generally and (3), especially, to carboxylated polystyrene latex particles. The advantages over the larger erythrocyte particles used in prior art kits in terms of lower graininess for the reagent as such and for negative test mixtures are inherent in the smaller particles of whatever material. It is preferred that the particles have a relatively narrow size distribution around the average, with a range of plus or minus 2% being preferred.

The antigen used in the first step of the invention may be any antigen that will be immunologically bound by an antibody of the type forming an immunological complex that acts as a receptor for RF (see the discussion below in relation to the gamma-globulin of the second step of the process). The invention is not limited to any specific antigen; however, protein antigens such as bovine serum albumin (BSA) are preferred because of their great availability and high binding efficiency to gamma-globulins that are easily available in high titers by means of innoculation.

It is preferred, however, that the protein antigens be chemically modified to increase their efficiency for eliciting the antibodies on innoculation and for binding antibodies during the incubation step (b). It should be appreciated that small molecules (e.g., drugs) have been chemically attached to proteins (especially BSA) in the past to elicit a raised production of antibodies to that small molecule on immunization. Such specific antibody production is not the purpose in the present invention, which is rather to enhance efficiency in number of binding sites on the BSA after it has been attached to the particle. Thus the specific chemical modification chosen is not critical and can be by any immunologically active group easily attached chemically to the protein, with organic chemical reagents being preferred, and substituted aromatic moieties being more preferred. One exemplary class of such moieties are the nitroaromatic moieties such as dinitrophenyl. Means of attaching such chemically modified moieties, and especially substituted aromatic groups to proteins are well known, e.g., by reaction between the free amines of lysine residues, free hydroxyls of tyrosine residues or free sulfhydryl of cysteine residues of the protein (BSA) and a halogen (e.g., flourine) on the precursor of the modifying moiety (e.g., fluorodinitrobenzene to produce dinitrophenyl) reacted with the protein under basic conditions. Such reactions are described in Methods in Immunology And Immunochemistry, vol. 1. pp. 128-33 (C. Williams et al., eds., 1967).

The step of attaching the antigen to the synthetic particle can be achieved by simple absorption or adsorption, and can also be achieved by chemical linking or other techniques. In the case of carboxylated polystyrene latex particles, chemical coupling to the protein (such as chemically modified BSA) via a carbodiimide reaction has proved adequate for the present purposes. The concentration of antigens on each particle is not critical except to provide a sufficient number of binding sites for antibodies to promote adequate formation of antigen/gamma-globulin immune complexes in the incubating step (b) and sufficiently high numbers for adequate binding of rheumatoid factor to such complexes upon use of the diagnostic reagent.

The second step of the process is to incubate the antigen-coated particle with a solution containing gamma-globulins directed against the antigen. The key to the step is that the gamma-globulins bind to the antigen binding sites on the coated particle to produce antigen/gamma-globulin immunological pairs. Most gamma-globulins will be active to binding by RF in the use of the reagent. Gamma-globulins of the IgG type are highly preferred because of their wide availability. Other gamma-globulins of the IgM type, IgA type, IgD type and IgE type are less preferred in pure form because of their lower availability. Rather than using specific types of gamma-globulin, however, it is more preferred to use mixtures, and especially naturally occurring mixtures obtained by immunization with the antigen, thus eliminating the necessity of a separation step. It is preferred that the antigen be from one species (e.g., such as BSA from cattle) and the antibodies from another species (such as whole serum from rabbits) and especially that the antibodies be obtained by immunizing animals of the second species (rabbits) with the antigen, and especially a chemically modified antigen from the first species (dinitrophenyl-modified BSA). The most preferred preparative technique (as illustrated in the examples) is to immunize a rabbit with chemically modified BSA, collect the rabbit serum and incubate that serum with particles coated with chemically modified BSA.

The conditions of the incubation steps are those that do not cause agglutination of the particles during such incubation step, but rather produce non-agglutinated particles having antigen/gamma-globulin immune complexes coated thereon. The formation of such complexes without agglutination can be controlled by using appropriate concentrations of serum globulins and antigen-coated particles so as to minimize gamma-globulins linking different coated particles to each other. In addition, however, it is preferred that some free antigen (such as chemically modified BSA) be present during the incubation step so as to reduce the multivalent sites of the gamma-globulins which could bind adjacent particles. Such free antigen may be that antigen, or preferably a portion thereof, which was present during the attaching step (a) but which did not attach to the synthetic particles. Representative conditions for the incubation step are a temperature of 4°–40° C. (especially 20°–25° C.), an incubation time of one minute or more (especially 1–2 hours), a pH of 5.7 to 8.7 (such as 7.2) and a weight percent latex of 1–10% (such as 5%). The only true limitations in the incubation step are to avoid denaturation and to avoid an excess of free antigens on some particles and excess of free antibody sites on the other particles that could produce, during storage or use, agglutination in the absence of rheumatoid factor. It is preferred, therefore, during the incubation step either to have a large excess of antibody or an excess of free antigen and antigen-coated particles, with an excess of free antigen and antigen-coated particles being preferred.

The third step of the process is to recover the particles having multiple antigen/gamma-globulin immune complexes thereon from suspension. Suitable recovery techniques include centrifugation, washing, dialysis or a combination thereof. The combination of centrifugation followed by washing illustrated in the examples is most preferred. As with the incubation step, conditions during recovery and subsequent storage of temperature or pH, that would cause freezing, denaturation or uncoupling of the immune complexes are preferably avoided. Accordingly, convenient storage conditions are 2°–10°

C. (such as 4° C.) and pH 6-9 (such as 7.2). The recovery step is preferably conducted so as to minimize residual free antigen and residual free antibody.

The fourth step of the process is to resuspend the coated particles in a storage-stable medium such as phosphate-buffered saline (or other conventional aqueous buffered solutions) at pH 7.2 containing 0.02% TRITON X-100 (or any similar surfactant used to stabilize latexes). It is preferred to add a preservative to such medium or suspension such as sodium azide.

The reagent of the present invention can be any prepared by the novel process. It can further be any suspension in storage-stable medium of a plurality of synthetic particles having multiple antigen/gamma-globulin immune complexes thereon as described in the brief description. The reagent need not necessarily be at the concentration to be used in the novel method, but may, for example, be at a higher concentration and be later diluted before use.

The diagnostic method of the present invention comprises incubating a serum sample with a plurality of synthetic particles having such multiple antigen/gamma-globulin immune complexes thereon. Such incubation can be initiated by combining an aliquot of the serum sample with the novel reagent, with either the serum sample or the reagent being diluted prior to incubation. For qualitative analysis, it is preferred to use a fixed concentration of the reagent and a fixed dilution (e.g., 1:10) of an aliquot of the serum sample. Incubation conditions can generally include room temperature (although somewhat higher or lower temperatures may be used), short times such as 1 to 5 minutes and preferably about 2 minutes, and incubation in a transparent container whereby agglutination after the incubation can be observed. While incubation may be conducted in an open or closed container, incubation in a well of an open test slide is preferred. Representative conditions are about 1-5 minutes in an open container (test well) with motion (generally a swirling motion by hand or mechanically), or about 10-120 minutes in a closed container (test tube) without motion. Using test slides with multiple wells, multiple samples may be analyzed simultaneously to qualitatively determine the presence of RF. Furthermore, a serum specimen may be diluted serially to multiple dilutions and the multiply diluted samples run simultaneously on the same test slide, each with an aliquot of the diagnostic reagent. In order to improve reliability of the test and of the evaluation thereof, it is preferred to simultaneously run additional incubations of the diagnostic reagent with a positive control serum (containing RF) and a negative controlled serum (substantially free of RF).

In general, the reagent can be made more sensitive (and also shortening the test period) by increasing the activity of immune complexes on the particles either by increasing the antigen level, the gamma-globulin level or, preferably, both. A balance is desired between sensitivity of the reagent for use and avoiding agglutination during reagent preparation (especially during incubation step (b)) or reagent storage. The reagent described in the Examples has proved stable for over a year, stored at 4° C.

The diagnostic kit of the present invention therefore includes the diagnostic reagent, and may include one or more of a positive controlled solution (containing RF), a negative control solution (substantially free of RF), a reusable incubation vessel (such as a test slide with multiple wells of suitable size) and a storage-stable diluent medium for diluting serum specimens. The term kit is intended, however, to include any assemblage of the novel diagnostic reagent and RF positive control solution, whether or not the other components are also present.

The present invention is illustrated by the following examples, which are not intended to limit the invention beyond the broad scope thereof set forth in the claims that follow.

EXAMPLES

(A) Preparation of Dinitrobenzene Conjugated Bovine Serum Albumin (DNB-BSA)

Bovine serum albumin (30%) (from Armour Pharmaceutical) was diluted to 10% using 0.1M $NaHCO_3$ buffer, pH 11.0. A 10% 1-fluoro-2,4-dinitrobenzene (FDNB) solution (W/V) in absolute alcohol was added dropwise to this 10% BSA solution. The mixture was stirred continuously and 5 ml of FDNB solution was added every hour for 6 hours until 3 g of FDNB was added for every 210 ml of 10% BSA solution. The reaction mixture was dialyzed against 4 l of PBS at 4° C. to remove unreacted FDNB.

(B) Immunization of Rabbits With DNB-BSA

The DNB-BSA immunogen (4 mg/ml) prepared as described in section A, above, was mixed with Freund's complete adjuvant in a ratio of 1:1 in a double barrel syringe. The emulsion (1 ml) was injected intramuscularly into the flank of the hind legs of each New Zealand white rabbit. At the third and fifth week, a booster shot of 1 ml of the immunogen (1 mg) which had been mixed with equal volume of Freund's incomplete adjuvant was given. At the seventh, eighth and ninth weeks, each rabbit was bled for 50 ml by cardiac puncture. The rabbit blood was allowed to clot and centrifuged. The serum was removed and centrifuged a second time to remove the remaining cells or debris. Sodium azide was added to 0.1% and the serum was stored frozen at −34° C.

(C) Coupling of BSA to Latex

To 5 ml of 9% carboxylated latex suspension in phosphate buffered saline (PBS) pH 6.0, 15 mg of 1-ethyl-3-(3-dimethylaminopropyl)-carbodiimide hydrochloride (ECDI) was added. After stirring at room temperature for 2 minutes, 10 mg of BSA was added. The suspension was diluted to five times original volume with PBS containing 0.02% Triton X-100. The latex was pelleted by centrifugation at 11,000×g for 15 minutes. The supernatant fluid was decanted and the latex was resuspended in 4.5 ml of PBS-Triton solution.

(D) Coupling of Mono-N-DNB-hexamethylenediamine (HMD-DNB) to BSA

The compound HMD-DNB was synthesized according to the method of Tolleshaug and Hannestad (Immunochemistry 12, 173–182, 1975). To 55.5 ml of 9% carboxylated latex in PBS, pH 6.0, 66 mg of the carbodiimide was added. After stirring at room temperature for 5 minutes, 88 mg of HMD-DNB in 3.2 ml of PBS was added. The suspension was stirred for 2 hours at room temperature. The latex suspension was diluted to 5 times original volume with PBS containing 0.02% Triton X-100. The latex was washed an additional eight times as described above. After the eighth wash the latex was resuspended in 50 ml of PBS-Triton solution and stored at 4° C.

(E) Coupling of DNB-BSA to Latex

The water soluble carbodiimide (364 mg) was added to 135 ml of 10% carboxylated latex suspension in PBS, pH 6.0. The mixture was stirred for 2 minutes and 550 mg of DNB-BSA (prepared as described in Section A, above) was added. The suspension was stirred for another 2 hours and then diluted to three times its original volume with PBS containing 0.02% Triton X-100. Uncoupled material was removed by centrifugation. The DNB-BSA latex was washed with PBS-Triton solution again and then stored as 5% suspension.

Preparation of Immune Complex (IC) Latex

Equal volumes of 5% antigen-coated latex (prepared as described in Section C or D or E, above) and an optimum dilution of rabbit antiserum DNB-BSA were mixed with stirring for 2 hours at room temperature. The latex suspension was diluted to three times the original volume with PBS which contained 0.02% Triton X-100. The mixture was centrifuged at 11,000×g for 45 minutes and the supernatant was decanted. The pellet was washed again and then resuspended in the PBS-Triton solution. The suspension was sonicated in a water bath sonicator for 2 minutes. Any large clumps which were not broken up by sonication were removed through a nylon mesh. Each product suspension was placed in 3 ml dropper bottles.

(G) Testing of Immune Complex Latex With RF Positive Samples

The serum to be tested was diluted 1:10 in PBS. One drop (approximately 50 μl) of the diluted serum was placed within the well on the glass slide. The 3 ml IC latex reagent bottle (containing the reagent to be tested) was shaken to suspend the latex. Then the bottle was held in a vertical position and one drop (approximately 30 μl) was placed within the well. The serum sample and the IC latex was mixed with a wooden stirrer and spread over the entire well. Then the slide was rocked gently with a rotary motion for two minutes, after which the wells were observed for latex agglutination using a high intensity fluorescent desk lamp. The agglutination was graded in the following manner:

N=No agglutination.
±=Trace agglutination
1, 2, 3, 4=Definite agglutination with the intensity increasing from 1 through 4.

EXAMPLE 1

Reactivity of RF positive serum with IC-latex which is made with BSA conjugated latex and rabbit antiserum.

| Dilution of RF Positive Serum #20 | Degree of Agglutination |
| --- | --- |
| 1:20 | 2 |
| 1:40 | 2 |
| 1:80 | 1 |
| 1:160 | ± |
| 1:320 | N |
| 1:640 | N |
| PBS | N |

EXAMPLE 2

Reactivity of RF positive serum with IC-latex which is made with HMD-DNP conjugated latex and rabbit antiserum.

| Dilution of RF positive Serum #105 | Degree of Agglutination |
| --- | --- |
| 1:40 | 4 |
| 1:80 | 4 |
| 1:160 | 4 |
| 1:320 | 3 |
| 1:640 | 1 |
| PBS | N |

EXAMPLE 3

Reactivity of RF positive serum with IC-latex which is made with DNB-BSA conjugated latex and rabbit antiserum.

| Dilution of RF positive Serum #20 | Degree of Agglutination |
| --- | --- |
| 1:20 | 4 |
| 1:40 | 3 |
| 1:80 | 2 |
| 1:160 | 1 |
| 1:320 | ± |
| 1:640 | N |
| PBS | N |

EXAMPLE 4

Serum samples were taken from over one hundred patients of a Rheumatologist and tested as in Example 3 using a 1:10 serum dilution. Thirty of the samples giving a positive reading at 1:10 dilution were retested at multiple dilutions (1:20, 1:40, 1:80, 1:160, 1:320, 1:640), with the reagent DNB-BSA conjugated latex of Example 3 and, as a control, with the erythrocyte-base reagent manufactured by the Wampole Laboratories division of Carter Wallace under their trademark "RHEUMATON". In each series of tests a titer was identified giving a positive test, with higher dilutions of the serum giving negative tests. If a positive test was obtained at 1:640 the test was repeated at 1:1280. The highest dilution (titer) giving a positive test is tabulated below for the thirty patient serum samples.

| Patient Serum Sample | Titer Using DNB-BSA Conjugated Latex Reagent | Titer Using Sheep Erythrocyte-Based Reagent |
| --- | --- | --- |
| 1 | 1:80 | 1:40 |
| 2 | 1:40 | 1:10 |
| 3 | 1:10 | 1:10 |
| 4 | 1:40 | 1:20 |
| 5 | 1:80 | 1:10 |
| 6 | 1:40 | 1:20 |
| 7 | 1:40 | 1:10 |
| 8 | 1:640 | 1:80 |
| 9 | 1:640 | 1:80 |
| 10 | 1:160 | 1:80 |
| 11 | 1:320 | 1:80 |
| 12 | 1:320 | 1:140 |
| 13 | 1:1280 | 1:160 |
| 14 | 1:80 | 1:20 |
| 15 | 1:40 | 1:40 |
| 16 | 1:80 | 1:40 |
| 17 | 1:40 | 1:20 |

-continued

| Patient Serum Sample | Titer Using DNB-BSA Conjugated Latex Reagent | Titer Using Sheep Erythrocyte-Based Reagent |
| --- | --- | --- |
| 18 | 1:640 | 1:160 |
| 19 | 1:320 | 1:80 |
| 20 | 1:320 | 1:80 |
| 21 | 1:1280 | 1:160 |
| 22 | 1:320 | 1:20 |
| 23 | 1:320 | 1:40 |
| 24 | 1:640 | 1:80 |
| 25 | 1:640 | 1:80 |
| 26 | 1:160 | 1:40 |
| 27 | 1:80 | 1:20 |
| 28 | 1:640 | 1:160 |
| 29 | 1:160 | 1:40 |
| 30 | 1:320 | 1:80 |

It can be seen from this Table that the novel reagent produced a greater titer (positive reading with more dilute serum sample) in twenty-eight of the thirty cases, and an equal titer in the other two cases. In addition, the false positive level for the normal population testing at 1:10 dilution was approximately one percent (1%) (based on the small number of samples tested).

What is claimed is:

1. A process for preparing a diagnostic reagent for Rheumatoid Factor which comprises the steps:
   (a) attaching to suspendable synthetic particles an antigen to form particles having multiple active antigen sites,
   (b) incubating a suspension of said particles having multiple active antigen sites with a solution containing a gamma-globulin to the antigen under conditions forming a substantially non-agglomerated suspension of particles having multiple antigen/gamma-globulin immune complexes thereon which are active as antigens to Rheumatoid Factor as antibody,
   (c) recovering said particles having multiple antigen/gamma-globulin immune complexes thereon from suspension, and
   (d) resuspending said particles having multiple antigen/gamma-globulin immune complexes thereon in a storage-stable medium.

2. The process of claim 1 wherein said synthetic particles are latex particles.

3. The process of claim 2 wherein said latex particles are carboxylated polystyrene latex particles.

4. The process of claim 3 wherein said carboxylated polystyrene latex particles are of average diameter between about 0.2 and about 2 micrometers.

5. The process of claim 3 wherein said carboxylated polystyrene latex particles are of average diameter between about 0.4 and about 1 micrometer.

6. The process of claim 1 wherein said synthetic particles are of average diameter between about 0.2 and about 2 micrometers.

7. The process of claim 1 wherein said synthetic particles are of average diameter between about 0.4 and about 1 micrometer.

8. The process of claim 1 wherein said antigen is a protein.

9. The process of claim 1 wherein said antigen is a protein modified by attachment of a small synthetic organic moiety.

10. The process of claim 9 wherein said small synthetic organic moiety is aromatic.

11. The process of claim 10 wherein said small synthetic aromatic organic moiety is substituted phenyl.

12. The process of claim 10 wherein said small synthetic aromatic organic moiety is dinitrophenyl.

13. The process of claim 1 wherein said solution containing a gamma-globulin contains a naturally occurring mixture of gamma-globulins obtained by immunization with said antigen.

14. The process of claim 13 wherein said solution containing a naturally occurring mixture of gamma-globulins is an animal serum of a first species.

15. The process of claim 14 wherein said antigen is a protein derived from a second animal species different from said first animal species.

16. The process of claim 13 wherein said solution containing a gamma-globulin further contains an antigen in solution which is competitive with the antigen binding sites on said particles for gamma-globulin binding sites, said antigen in solution being present in an amount sufficient to prevent substantial agglomeration during said incubating step (c).

17. The process of claim 1 wherein said particles having multiple antigen/gamma-globulin immune complexes thereon are recovered by centrifugation.

18. A diagnostic reagent for the detection of Rheumatoid Factor produced by the process of claim 1.

19. A diagnostic reagent for Rheumatoid Factor comprising a suspension in a storage-stable medium of a plurality of synthetic particles having multiple antigen/gamma-globulin immune complexes thereon wherein the antigen is attached to the synthetic particle and wherein the antigen/gamma-globulin immune complexes are effective as antigens to Rheumatoid Factor as antibody.

20. The diagnostic reagent of claim 19 wherein said synthetic particles are latex particles.

21. The diagnostic reagent of claim 20 wherein said latex particles are carboxylated polystyrene latex particles.

22. The diagnostic reagent of claim 21 wherein said carboxylated polystyrene latex particles are of average diameter between about 0.2 and about 2 micrometers.

23. The diagnostic reagent of claim 19 wherein said synthetic particles are of average diameter between about 0.2 and about 2 micrometers.

24. The diagnostic reagent of claim 19 wherein said antigen is a protein modified by attachment of a small organic moiety.

25. The diagnostic reagent of claim 19 wherein the antigen/gamma globulin immune complexes have been formed from an antigen derived from a first animal species and from a gamma globulin to said antigen derived by immunizing an animal of a second species with said antigen.

26. A diagnostic kit comprising the diagnostic reagent of claim 19 and a positive control solution containing Rheumatoid Factor.

27. The diagnostic kit of claim 26 further comprising a negative control solution substantially free of Rheumatoid Factor.

28. The diagnostic kit of claim 26 further comprising a diluent solution for diluting aliquots of serum samples to different dilution levels before incubating with an aliquot of said diagnostic reagent.

29. The diagnostic kit of claim 26 wherein said synthetic particles are carboxylated polystyrene latex particles.

30. The diagnostic kit of claim 29 wherein said carboxylated latex particles are of average diameter between about 0.2 and about 2 micrometers.

31. The diagnostic kit of claim 26 wherein said synthetic particles are of average diameter between about 0.2 and about 2 micrometers.

32. The diagnostic kit of claim 26 wherein the antigen/gamma globulin immune complexes have been formed from an antigen derived from a first animal species and from a gamma globulin to said antigen derived by immunizing an animal of a second species with said antigen.

33. A diagnostic method for the detection of Rheumatoid Factor in a serum sample which comprises incubating the serum sample with a plurality of synthetic particles having multiple antigen/gamma-globulin immune complexes thereon wherein the antigen is attached to the synthetic particle and wherein the antigen/gamma-globulin immune complexes are effective as antigens to Rheumatoid Factor as antibody, whereby the particles will agglomerate if a sufficient quantity of Rheumatoid Factor is present in the serum sample.

34. The diagnostic method of claim 33 wherein a suspension of said particles is combined with an aliquot of said serum sample to initiate the incubation.

35. The diagnostic method of claim 34 wherein a plurality of aliquots of a suspension of said particles are separately combined with a plurality of diluted aliquots of said serum sample, of differing dilutions, to initiate the incubation.

36. The diagnostic method of claim 33 wherein the incubation is conducted for between about 1 and about 5 minutes in an open container with motion.

37. The diagnostic method of claim 33 wherein the incubation is conducted for between about 10 and about 120 minutes in a closed container without motion.

38. The diagnostic method of claim 33 wherein the antigen/gamma globulin immune complexes have been formed from an antigen derived from a first animal species and from a gamma globulin to said antigen derived by immunizing an animal of a second species with said antigen.

* * * * *